Figure 1:
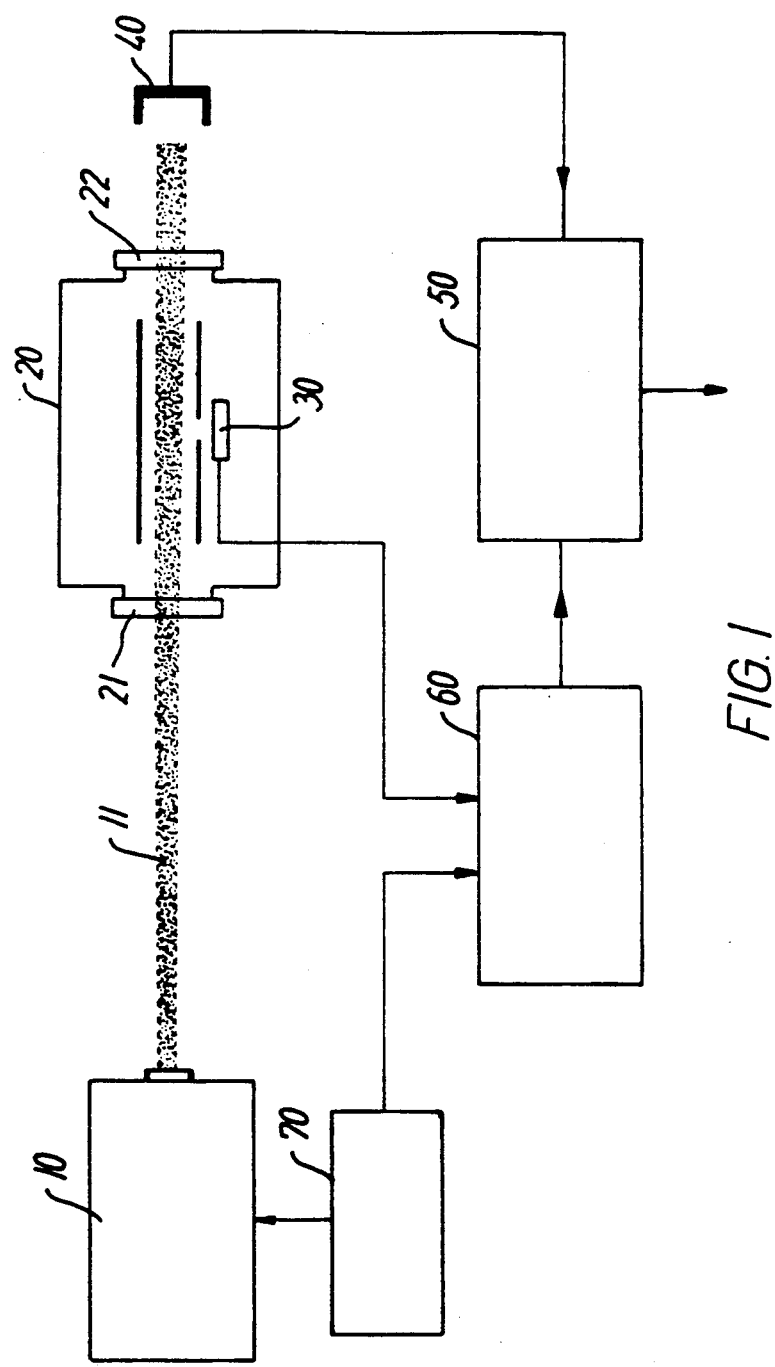

United States Patent [19]

Hammerich et al.

[11] Patent Number: 5,159,411
[45] Date of Patent: Oct. 27, 1992

[54] METHOD AND APPARATUS FOR THE DETECTION OF A GAS USING PHOTOACOUSTIC SPECTROSCOPY

[75] Inventors: Mads Hammerich, Hilleroed; Jes Henningsen, Stenloese, both of Denmark; Ari Olafsson, Reykjavik, Iceland

[73] Assignee: FLS Airloq A/S, Denmark

[21] Appl. No.: 663,852

[22] PCT Filed: Sep. 12, 1989

[86] PCT No.: PCT/DK89/00211
§ 371 Date: May 8, 1991
§ 102(e) Date: May 8, 1991

[87] PCT Pub. No.: WO90/02935
PCT Pub. Date: Mar. 22, 1990

[30] Foreign Application Priority Data

Sep. 12, 1988 [DK] Denmark .................... 5066/88

[51] Int. Cl.⁵ .................................. G01N 21/17
[52] U.S. Cl. ............................ 356/432; 356/437
[58] Field of Search ............ 356/432 T, 437, 432; 250/343

[56] References Cited

U.S. PATENT DOCUMENTS

| | | | |
|---|---|---|---|
| 3,948,345 | 4/1976 | Rosencwaig | 356/432 T |
| 4,058,725 | 11/1977 | Aine | 250/343 |
| 4,457,162 | 7/1984 | Rush et al. | 73/24.01 |
| 4,740,086 | 4/1988 | Oehler et al. | 356/432 T |

OTHER PUBLICATIONS

Wood et al., "Effects of 10.6-μ Laser Induced Air Chemistry on the Atmospheric Refractive Index", *Applied Optics*, vol. 10, No. 8 (Aug. 1971), pp. 1877–1884.

*Primary Examiner*—Richard A. Rosenberger
*Attorney, Agent, or Firm*—Brumbaugh, Graves, Donohue & Raymond

[57] ABSTRACT

In a process for the detection of a first gas in a gas mixture comprising a second gas, the absorption spectre of which interferes with the absorption spectre of the first gas, a photoacoustic measurement is carried out in the presence of a third gas which in combination with the first or the second gas exhibits kinetic cooling. During measurement the gas mixture is influenced by pulsating laser light having a constant repetition frequency where the frequency of the laser light is varied gradually. The measurement comprises at least one detection of the phase of the photoacoustic signal as a function of the laser light frequency. The invention further relates to an apparatus for carrying out the invention.

9 Claims, 4 Drawing Sheets

METHOD AND APPARATUS FOR THE DETECTION OF A GAS USING PHOTOACOUSTIC SPECTROSCOPY

The invention relates to a method and apparatus for the detection of a gas using photoacoustic spectroscopy.

All gases have characteristic absorption spectra disclosing the ability of the material to absorb energy as a function of the wavelength of a direct influx of energy. This absorption spectrum is characteristic for each specific gas and may be considered a sort of fingerprint for the gas. Thus, a specific gas in a gas mixture may be detected by measuring the energy absorption of the gas mixture at selected wavelengths of energy where the gas has a high absorption. A method and an apparatus for such measuring is known from U.S. Pat. No. 4,740,086. Another very appropriate measurement method for measuring such absorption is photoacoustic spectroscopy as mentioned for instance by A. G. Bell in "Philosophical Magazine" 11, 510 (1981). According to this method the gas mixture is influenced by a pulsated energy source, e.g. a laser, c.f. E. L. Kerr and J. G. Atwood, "Applied Optics" 7, 915 (1968). The energy absorption of the gas mixture will cause a pressure increase and a pressure decrease, respectively, proportional to the absorption, the gas being heated during absorption of the energy and being cooled again when releasing the energy absorbed to the surroundings. The absorption may thus be recorded using a pressure transducer wherein the pressure is proportional to the absorption.

However, this measurement method gives rise to problems e.g. in case of interference between the absorption spectra of two gases. In that event it is very difficult to distinguish the absorption of each of the specific gases from each other.

This problem is known in particular from measurements carried out on atmospheric gas mixtures using a $CO_2$ laser. Herein the large amount of $CO_2$ in the gas mixture in combination with the particularly intensive absorption ability of $CO_2$ at the wavelengths of radiation which may be generated with a $CO_2$ laser to a particularly high degree obstructs the detection of less dominant gases, c.f. U.S. Pat. No. 4,457,162.

As disclosed in the article "Selectivity in Optoacoustic Trace Gas Monitoring with Waveguide $CO_2$ lasers": 11th International Conference on Infrared and Milimeter Waves, Tirreria, Pisa, 24–24 October 1086, the selectivity as regards different gases may be increased by letting the laser scan a wavelength range around a centre wavelength instead of measuring the photoacoustic amplitude at some of the fixed wavelengths of the laser. The laser is pulsated in a conventional manner where the radiation emitted within each pulsation has a constant wavelength, but the wavelength is changed in the course of several pulsations. Combination of this scanning with a reduced pressure in the measurement chamber, thus concentrating the absorption to a narrowed wavelength range, has resulted in a significantly increased selectivity. As to measurement in e.g. atmospheric environments, however, this method is still far from satisfactory, the $CO_2$ content of the gas mixture still drowning the photoacoustic signals from less dominant gases.

It is the object of the invention to provide a method for the detection of a first gas in a gas mixture through photoacoustic spectroscopy, wherein the gas mixture further comprises a second gas the absorption spectrum of which interferes with the absorption spectrum of the first gas, wherein the gas mixture is irradiated by pulsating laser light having a constant pulsation frequency and therefore a uniform wavelength during the measurement and wherein the wavelength of the laser light is varied gradually and wherein the measurement comprises at least one reading of the phase of the photoacoustic signal as a function of the uniform wavelength during measurement wherein, however, the above inconveniences are eliminated.

This is achieved whereby a photoacoustic measurement is carried out in the presence of a third gas in the gas mixture, said third gas being present in the gas mixture or being added to the mixture immediately before the measurement and exhibiting kinetic cooling in combination with the first or the second gas. Thus, the phenomenon "kinetic cooling" is used to phase shift a partial absorption contribution in the gas mixture thereby permitting detection of the presence of a gas in substantially lower concentrations than it has been possible so far by regarding the phase course as a function of the wavelength.

Kinetic cooling is subject to more detailed discussion in the article: "F. G. Gebhardt & D. C. Smith Kinetic Cooling of a Gas by Absorption of $CO_2$ Laser Radiation" Appl. Phys. Lett. 20, 129, 1972, but in summary it comprises the following: Generally the laser light will excite a part of the molecules which have an absorption wavelength close to that of the laser wavelength when the light reaches the gas in the measuring cell. These molecules are excited to a higher energy state when they collide with other molecules. This higher energy level is unstable and the energy will be released to the surroundings in the form of heat. This heat generates pressure changes which may be recorded by a pressure transducer due to the pulsation of the laser. For certain combinations of molecules it applies that their high energy levels are close to each other and therefore they are in resonance. Here an excited molecule may lose an energy amount to another molecule which corresponds to twice the amount originally received from the photon. Thereby, the first molecule is in an unstable state, wherein it has an energy deficit as compared to the stable state. The molecule compensates for this through the absorption of energy from the surroundings. Therefore, in this case a subsequent cooling of short duration of the system is recorded when energy is supplied thereto.

By detecting the amplitude of the absorption, too, the method may also be used to carry out improved amplitude measurement by photoacoustic spectroscopy since the phase signal may also be used for the detection in the amplitude signal of such information which is overridden by other information having higher amplitude.

An appropriate special embodiment of the method may be used for the measurement of atmospheric gas mixtures resulting from e.g. combustion processes or from particularly exposed environments where it is desirable to detect pollution gas. In particular it is the absorption into $CO_2$ which interferes with the measurement and it is therefore desirable to eliminate part of this contribution. $CO_2$ exhibits distinct kinetic cooling in connection with $N_2$, and $N_2$ being present already in atmospheric gas mixtures in high concentrations, the $CO_2$ contribution may be eliminated to a large extent simply by detecting the phase course of the photoacoustic signal as a function of the wavelength.

The apparatus for carrying out the method is characterized in that the wavelength of the laser is settable within certain wavelength intervals, and in that the electronic circuit comprises phase detection means constructed to record the phase course of the acoustic signal as a function of the wavelength of the laser within a wavelength over which the absorption spectrum of the gas to be measured changes measurably.

Figure 2:
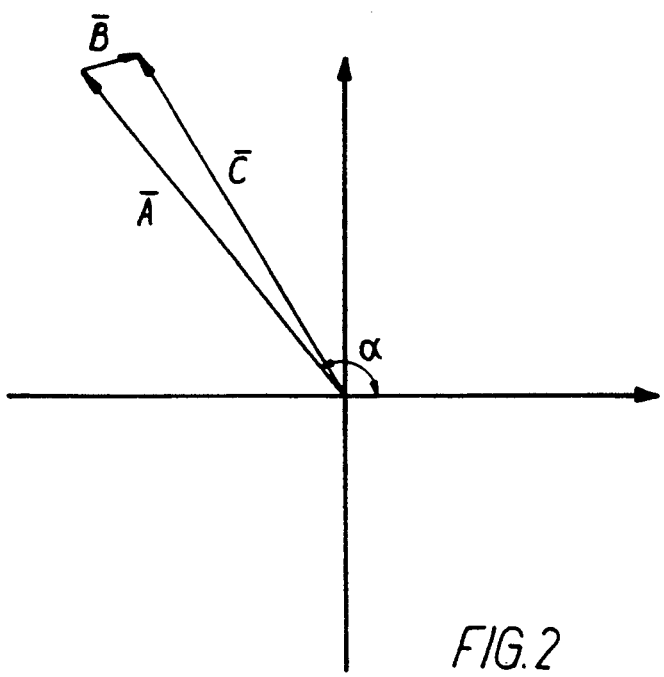
Figure 3:
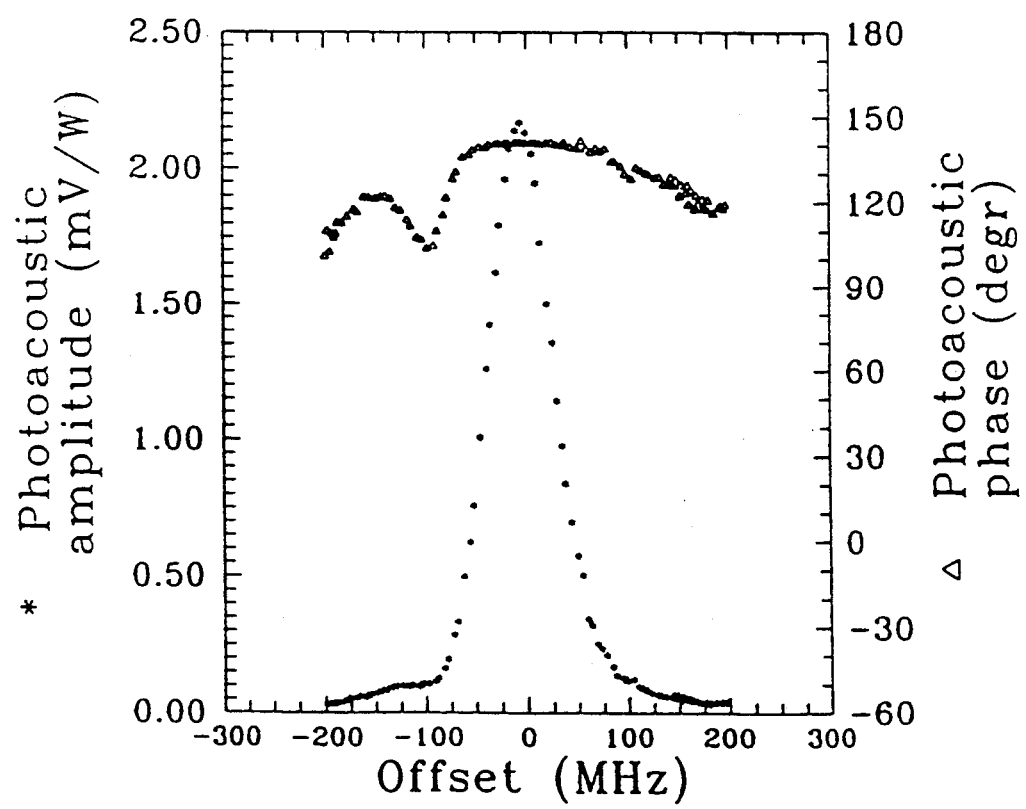
Figure 4:
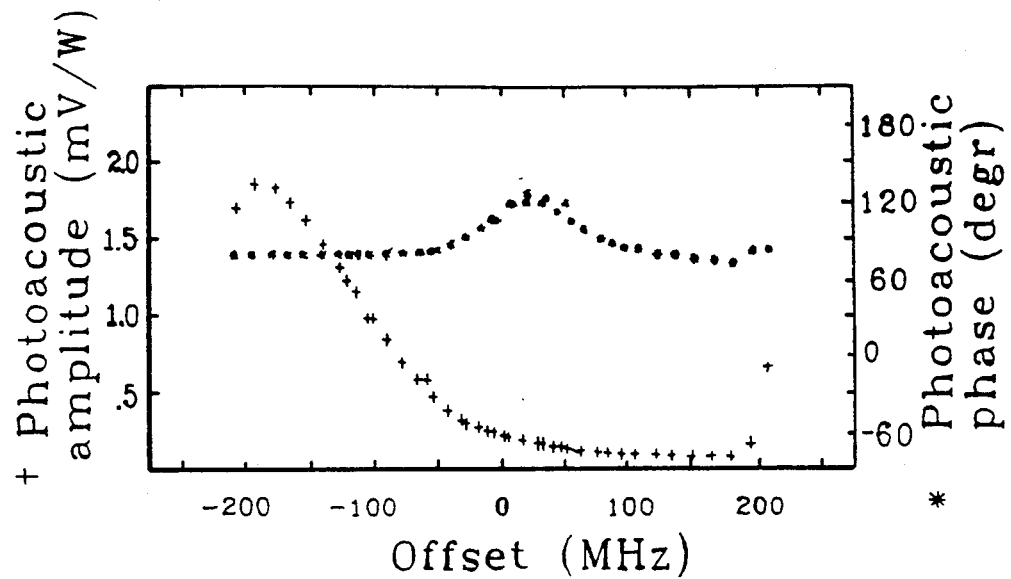
Figure 5:
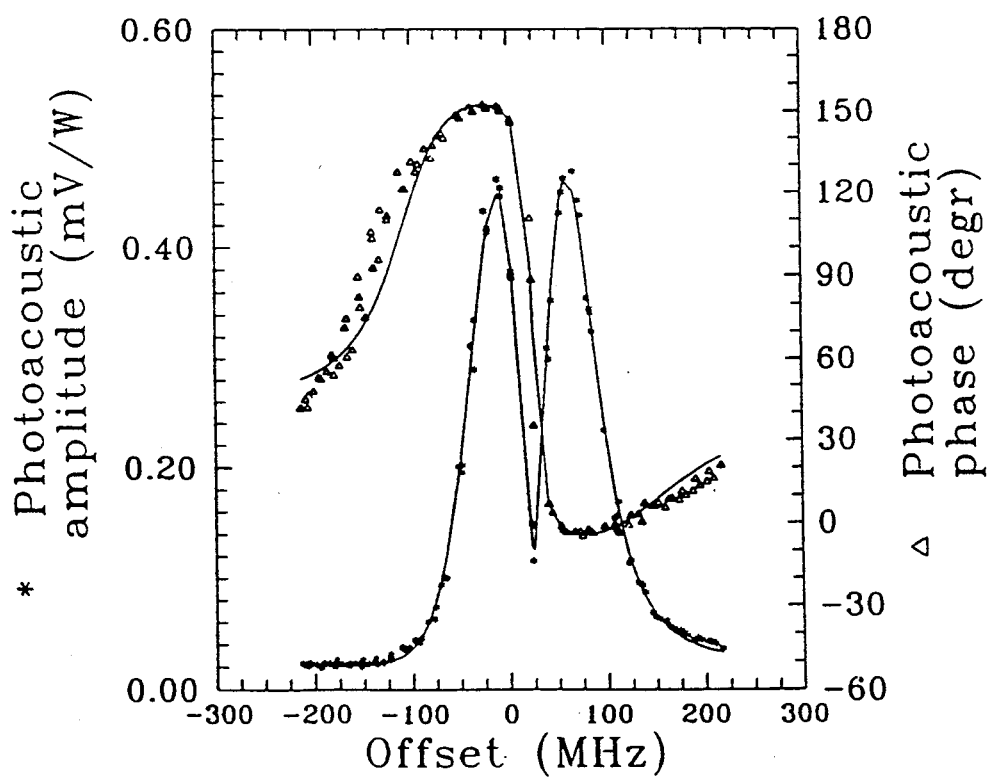
Figure 6:
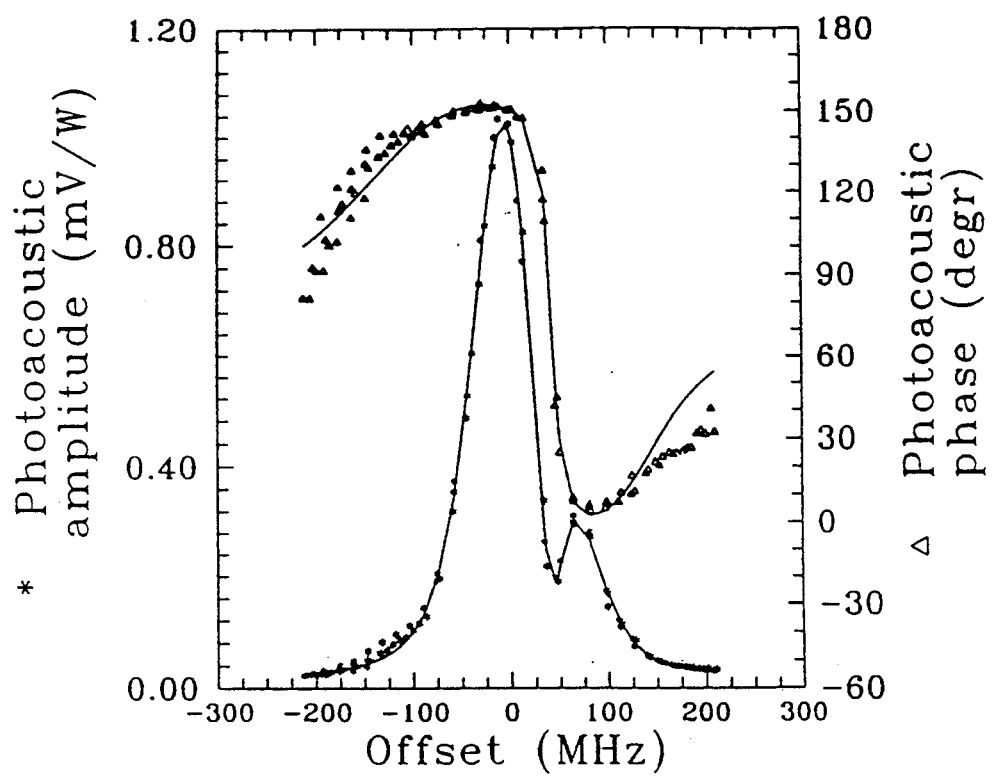
Figure 7:
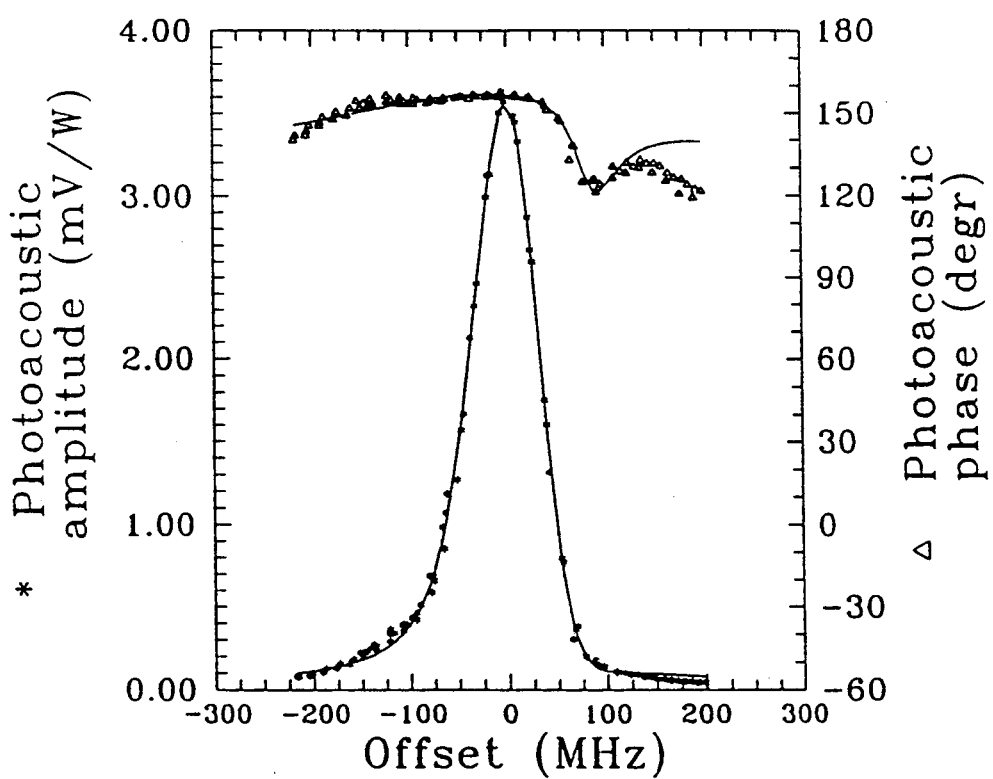

In the following the invention will be described with reference to the accompanying drawings, wherein:

FIG. 1 is a schematic view of the apparatus for carrying out the method according to the invention, FIG. 2 shows the summation of the signal in vector form, FIGS. 3 and 4 show absorption spectra for gas mixtures having trace elements as measured according to the invention, FIGS. 5, 6 and 7 show absorption spectra for a trace element which is present in an increasing concentration of interfering gases.

FIG. 1 illustrates the photoacoustic gas detection system comprising a laser 10 which, according to a preferred embodiment, is a $CO_2$ laser due to the high output of such a laser. The laser 10 may be set to several wavelengths which will be referred to in the following as center wavelengths. Furthermore, the laser 10 may be tuned within a certain range of wavelengths to either side of the center wavelength. Each center wavelength and the associated tuning range will be referred to as a spectral window. The $Co_2$ laser operates in such a way that its intensity varies periodically in time, with a constant pulsation or modulation frequency. This is achieved either by using a laser which emits pulsed radiation, or by using a laser emitting continuous wave radiation, the radiation being subsequently modulated by an external modulator or a chopper. In the following the constant pulsation or modulation frequency will be referred to as the pulsation frequency. The pulsation frequency is chosen according to the gas being measured and will generally be within the frequency range characteristic of acoustics, i.e. within the response limits of a conventional microphone.

The laser is passed through a cell 20 containing a sample of the gas to be scanned for trace elements. According to the preferred embodiment the cell 20 is constructed as an acoustic resonator in which a microphone 30 is mounted. The resonance frequency of the acoustic resonator is chosen to coincide with the laser radiation pulsation frequency. The light enters through a window 21 in the measuring cell 20. The gas within the cell will absorb part of the light and also part of the radiation, which is subsequently converted to heat pulses and pressure pulses synchronous with the pulses of the laser radiation.

The pressure pulses are picked up by the microphone 30 and converted to an electric signal which is proportional to the amount of laser radiation absorbed in the cell. That part of the laser radiation which is not absorbed passes through the cell to a power detector 40, where it is converted to an electric signal. This signal represents the original laser power minus the power being absorbed in the cell. Under conditions typical of trace gas monitoring, the absorbed radiation will represent a very small fraction of the indicent radiation, and the signal generated by the laser power detector 40 may then be taken to represent the incident radiation.

In a dual channel lock-in amplifier 60, the signal generated by the microphone 30 is divided into two equal parts. One part is multiplied by a periodic signal having the same period and phase as the microphone signal, while the other part is simultaneously multiplied by a periodic signal also having the same period as the microphone signal, but differing in having its phase displaced by 90 degrees. Subsequently, the two product signals are integrated over a period. The resulting figures are the real and the imaginary part of a complex number representing the magnitude and the phase of the absorption signal. The two periodic signals are derived from a trigger 70, which also controls the pulsation frequency of the laser.

In addition to being proportional to the amount of laser power being absorbed in the cell, the microphone signal is also proportional to the amount of radiation incident upon the cell. In order to remove the latter dependence the magnitude of the output signal from the lock-in amplifier 60 is divided by the signal generated by the laser power detector 40. This operation is carried out in an analog ratio meter or in a digital computer 50.

Measurements of the photoacoustic magnitude and phase are carried out at least at one laser wavelength for which the gas to be measured has a measurable absorption. More detailed information is obtained by carrying out measurements at several discrete wavelengths, and a maximum of information is obtained by measuring repeatedly while the laser wavelength is scanned slowly over the entire spectral window, covering regions where the gas to be measured absorbs, as well as regions where this is not the case. The data may be printed out by a plotter or displayed on a monitor (not shown) yielding an absorption spectrum of the gas.

Implementation of a catalogue of the absorption spectra of the various gases permits quantitative determination of the concentrations of the gases constituting a given sample. In case of e.g. a sample comprising atmospheric air and some polluting trace elements the fact that e.g. $CO_2$ and $N_2$ jointly exhibit kinetic cooling may be exploited. If the laser radiation is periodically pulsed, the kinetic cooling corresponds to a phase delay of the photoacoustic signal relative to the phase of the exciting laser radiation. The actual magnitude of this phase delay depends on the gas composition and the total pressure as well as on the pulsation frequency. The choice of pulsation frequency and total cell pressure is thus dictated by the characteristics of the monitoring problem. For $CO_2$ and $N_2$ a pulsation frequency of about 700 c/s (or Hz) is found convenient leading to a phase delay of typically 120 degrees for the microphone signal originating from absorption by $CO_2$.

When scanning the laser wavelength over a spectral window, the microphone signal will in a realistic monitoring situation receive contributions from the following sources:

(a) Absorption in the cell windows 21, 22 and absorption of radiation scattered to the walls of the cell 20.

(b) Absorption from tails of spectrally distant water vapor absorption lines.

(c) Absorption from spectrally close absorption lines of molecules not exhibiting kinetic cooling.

(c) Absorption from spectrally close absorption lines of molecules not exhibiting kinetic cooling.

(d) Absorption from spectrally close absorption lines of molecules exhibiting kinetic cooling.

These different contributions may be difficult to disentangle solely on the basis of the overall magnitude of the microphone signal, but by including the phase information valuable additional information is obtained. Contribution above source (a) will lead to a coherent background with a phase which is essentially constant across the spectral window, and in general different from the phases of the contribution sources (b), (c) and (d). The phase of contribution from source (b) will be constant over the spectral window. Finally, the contributions from sources (c) and (d) will display a characteristic variation over the spectral window, but with a mutual phase shift. In the following this is illustrated explicitly for a number of cases.

FIG. 2 shows the vector summation of a strong signal A (which may be the result of the presence of $CO_2$ and $N_2$) and a weak signal B (e.g. from $SO_2$). While the presence of B causes little change in the magnitude of the total signal C, an evident change of several degrees may be detected in its phase.

FIG. 3 illustrates a situation where the trace element ($SO_2$) not exhibiting kinetic cooling is present on a strong background of a molecule exhibiting such cooling ($CO_2$ in combination with $N_2$). It appears that the amplitude curve (marked with *) is similar to a single absorption line profile for $CO_2$ with only ambiguous indications of a trace element being present. Observation of the phase curve (marked with $\Delta$), however, clearly reveals the presence of a trace element in the gas mixture. Moreover, the dip in the phase curve originating from the trace element is located at an optical frequency which is about $-110$ Mc/s (MHz) offset the center frequency of the window. Referring to the aforementioned catalogue of absorption spectra for various gases, this strongly suggests that the trace element is $SO_2$.

FIG. 4 illustrates the converse situation where a trace element exhibiting kinetic cooling ($CO_2$ in combination with $N_2$) is present on a strong background of a molecule not exhibiting such cooling ($NH_3$). The maximum of the curve originating from $N_3$ (marked with +) is centered at an optical frequency which is about $-190$ Mc/s (or MHz) offset the center of the window. While the overall magnitude of the microphone signal does not reveal the presence of a trace gas the phase curve (marked with *) clearly indicates the presence of $CO_2$ absorbing at the center of the window.

Since the method permits a precise determination of the absorption wavelengths of the molecules, a catalogue of the absorption spectra of molecules will permit the identification as well as the quantitative determination of the concentration of trace gas molecules from measurements over one or more spectral windows.

FIGS. 5, 6 and 7 illustrate how the absorption of $SO_2$ is gradually overshadowed by an increasing concentration of $CO_2$ in the gas mixture. FIG. 5 corresponds to 1% $CO_2$ and 500 ppm (parts per million) $SO_2$ in a background of $N_2$. The magnitude of the microphone signal (marked with *) clearly shows the presence of two lines, and the phase (marked with $\Delta$) is still 150 degrees. In FIG. 7, the $CO_2$ concentration has been raised to 5%, the $SO_2$ concentration being still 500 ppm. Now it is in all essential impossible to infer the presence of $SO_2$ from the magnitude of the microphone signal (marked with *), whereas the phase curve (marked with $\Delta$) still clearly reveals the presence of the second gas. Furthermore, the location of a dip in the phase curve at a frequency +90 Mc/s (or MHz) offset the center of the window in conjunction with the aforementioned catalogue suggests the trace element to be $SO_2$ (note that the location of the dip originating from $SO_2$ is different from the one seen in FIG. 3 because FIGS. 5, 6 and 7 refer to a different spectral window).

What is claimed is:

1. A method for the detection of a first gas in a gas mixture through photoacoustic spectroscopy, wherein the gas mixture further comprises a second gas the absorption spectrum of which interferes with the absorption spectrum of the first gas, wherein the gas mixture is irradiated by pulsating laser light having a constant pulsation frequency and therefore a uniform wavelength during the measurement and wherein the wavelength of the laser light is varied gradually and wherein the measurement comprises at least one reading of the phase of the photoacoustic signal as a function of the uniform wavelength during measurement, characterized in that a photoacoustic measurement is carried out in the presence of a third gas in the gas mixture, said third gas being present in the gas mixture or being added to the mixture immediately before the measurement and exhibiting kinetic cooling in combination with the first or the second gas.

2. A method according to claim 1, characterized in that, during the measurement, the gas mixture is provided in a measurement chamber where the pressure is reduced as compared to the atmospheric pressure.

3. A method according to any one of claims 1 or 2, characterized in that, during measurement, the gas mixture is provided in a measurement chamber which is constructed as an acoustic resonator and in that the resonance frequency of the measurement chamber is substantially identical with the pulsation frequency of the laser light.

4. A method according to claim 3, characterized in that the measurement also comprises the reading of the amplitude of the photoacoustic signal as a function of the wavelength of the laser light.

5. A method according to claim 3, characterized in that the absorption of the gas mixture is measured both as to amplitude and phase at a minimum of one wavelength at which the first gas exhibits absorption, that the third gas is added to the gas mixture which third gas coacts with either the first or the second gas in such a way that they exhibit kinetic cooling, that the absorption of the gas mixture is measured again at the same wavelength, and that the minimum of two amplitude and phase measurements are combined to determine the absorption amplitude of the first gas.

6. A method according to any one of the claims 1-2, characterized in that the measurement also comprises the reading of the amplitude of the photoacoustic signal as a function of the wavelength of the laser light.

7. A method according to claim 6, characterized in that the absorption of the gas mixture is measured both as to amplitude and phase at a minimum of one wavelength at which the first gas exhibits absorption, that the third gas is added to the gas mixture which third gas coacts with either the first or the second gas in such a way that they exhibit kinetic cooling, that the absorption of the gas mixture is measured again at the same wavelength(s), and that the minimum of two amplitude and phase measurements are combined to determine the absorption amplitude of the first gas.

8. A method according to any one of claims 1-2, characterized in that the absorption of the gas mixture is measured both as to amplitude and phase at a minimum of one wavelength at which the first gas exhibits absorption, that the third gas is added to the gas mixture which third gas coacts with either the first or the second gas in such a way that they exhibit kinetic cooling, that the absorption of the gas mixture is measured again at the same wavelength(s), and that the minimum of two amplitude and phase measurements are combined to determine the absorption amplitude of the first gas.

9. An apparatus for carrying out the method according to claim 1 comprising in combination a laser, means for pulsation of the laser light, a measuring cell exhibiting acoustic resonance at a frequency which is substantially identical with the pulsation frequency of the laser light, a detector for the detection of the radiation passing through the measuring cell, a detector for the detection of an acoustic signal from the measuring cell, and an electronic measurement circuit for processing the signal from the detectors, characterized in that the wavelength of the laser is settable within certain wavelength intervals, and in that the electronic circuit comprises phase detection means constructed to record the phase course of the acoustic signal as a function of the wavelength of the laser within a wavelength interval over which the absorption spectrum of the gas to be measured changes measurably.

* * * * *